(12) United States Patent
Nye et al.

(10) Patent No.: US 9,108,991 B1
(45) Date of Patent: Aug. 18, 2015

(54) PROCESS FOR REDUCING THE LEVEL OF CHORIDE IN CHLOROSILANE DIRECT PROCESS HYDROLYZED SUBSTRATE

(71) Applicant: Momentive Performance Materials Inc., Waterford, NY (US)

(72) Inventors: Susan A Nye, Feura Bush, NY (US); David S Schlitzer, Ballston Spa, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/456,384

(22) Filed: Aug. 11, 2014

(51) Int. Cl.
*C07F 7/18* (2006.01)
*C07F 7/08* (2006.01)

(52) U.S. Cl.
CPC ............... *C07F 7/0832* (2013.01); *C07F 7/089* (2013.01)

(58) Field of Classification Search
USPC .......................................... 556/435, 457, 462
See application file for complete search history.

(56) References Cited

U.S. PATENT DOCUMENTS

| 4,408,030 | A | | 10/1983 | Marko |
| 5,175,330 | A | | 12/1992 | Speier |
| 5,238,661 | A | * | 8/1993 | van Ghemen et al. .......... 423/81 |
| 5,374,310 | A | | 12/1994 | Bunce et al. |
| 5,876,609 | A | | 3/1999 | White et al. |

* cited by examiner

*Primary Examiner* — Sudhakar Katakam
*Assistant Examiner* — Pancham Bakshi
(74) *Attorney, Agent, or Firm* — Dominick G. Vicari; Joseph S. Ostroff

(57) ABSTRACT

The present invention relates to a process for providing a low-chloride hydrolyzate comprising contacting an acid or base hydrolyzed substrate of a chlorosilane direct process residue with nitric acid to provide a hydrolyzate with a chloride content of less than about 1.8% by weight. The process of present invention is especially useful in cement kilns and smelter operation.

14 Claims, 1 Drawing Sheet

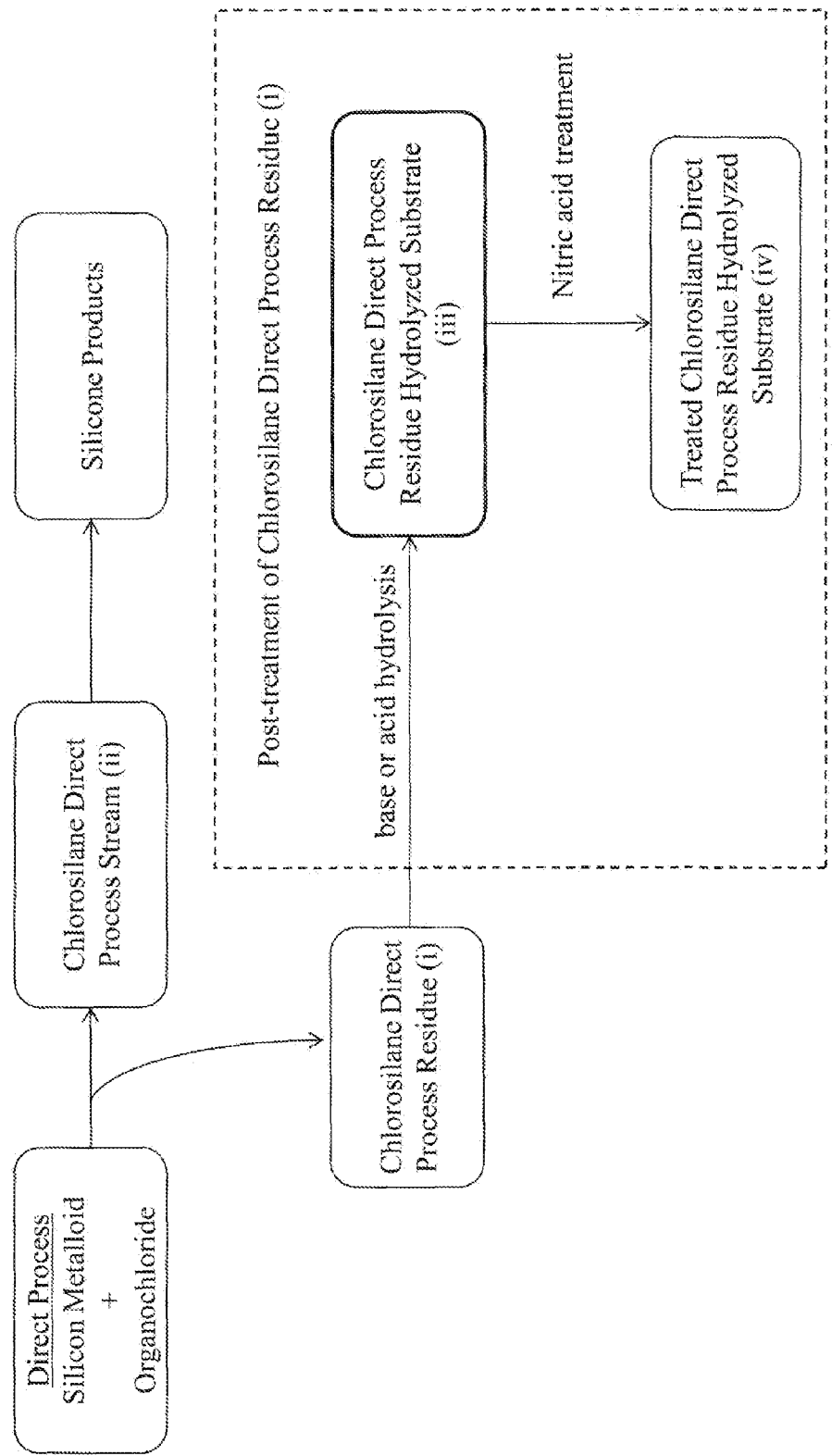

PROCESS FOR REDUCING THE LEVEL OF CHORIDE IN CHLOROSILANE DIRECT PROCESS HYDROLYZED SUBSTRATE

FIELD OF THE INVENTION

The present invention relates to a process for reducing the level of chloride in a chlorosilane direct process residue hydrolyzed substrate. Particularly, the invention relates to a process for reducing the level of chloride to less than 0.5% by weight on a dry basis.

BACKGROUND OF THE INVENTION

The manufacture of silicone products generates residue that can present serious problems in its safe and environmentally acceptable disposal. A variety of methods are known for treating chlorosilane direct process residue. However, there is a persistent high level of chloride in the treated chlorosilane residue.

Methods for reducing the level of chloride in chlorosilane residue are also known. However, the chloride level of treated residue is still too high limiting or preventing the use of residue in cement kilns. Additionally, smelter operations impose financial penalties for chlorosilane residues with chloride levels above 0.1%.

SUMMARY OF THE INVENTION

In accordance with one aspect of the invention, there is provided a process for providing a low-chloride hydrolyzate comprising contacting an acid or base hydrolyzed substrate of a chlorosilane direct process residue with nitric acid to provide a hydrolysate with a chloride content of less than about 1.8% by weight. In certain embodiment, the process of the present invention effectively reduces the level of chloride to less than 0.5% by weight. The treated chlorosilane direct process residue hydrolyzed substrate of the present invention is especially useful in cement kilns and smelter operation.

BRIEF DESCRIPTION OF THE FIGURE

FIG. 1 is a flowchart of the use of a chlorosilane direct process stream and the subsequent treatments of the chlorosilane direct process residue.

DETAILED DESCRIPTION OF PREFERRED EMBODIMENTS

The present invention provides a process to effectively reduce the level of chloride in the chlorosilane residue to offer an economical and environmentally sound utilization of the residue stream.

In the specification and claims herein, the following terms and expressions are to be understood as indicated herein below.

It will also be understood that any numerical range recited herein is intended to include all sub-ranges within that range and any combination of end points of said ranges or sub-ranges.

All methods described herein may be performed in any suitable order unless otherwise indicated or clearly contrary to context. The use herein of any and all examples or exemplification language (for example, such as), is intended merely to better illustrate the invention and does not pose a limitation on the scope of the invention unless otherwise claimed. No language in the specification should be construed as indicating any non-claimed element as essential to the practice of the invention.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Referring to FIG. 1, chlorosilane direct process residue (i) can be obtained from what is commonly called the "direct process" where silicon metalloid is reacted with organochloride to produce chlorosilane direct process stream (ii) and byproduct chlorosilane direct process residue (i). For example, an organochloride such as methyl chloride is reacted with silicon metalloid to form organochlorosilanes. Chlorosilane direct process residue (i) has little or no commercial value.

Chlorosilane direct process residue (i) can include, for example, high-boiling liquids (>75° C.), distillation residues, chlorosilanes, suspended silicon powder, elevated levels of copper, zinc and tin, as well as a variety of other metals.

The major components of chlorosilane direct process residue (i) are summarized in Table 1. These compositions are considered typical for by-product streams, but considerable batch to batch variation can exist. The liquid portion of the residue may include numerous high boiling multi-functional alkylchlorosilanes, alkylchlorocarbosilanes, alkylchlorosiloxanes and alkylchlorooligosilanes, where the alkyl substituent is predominantly methyl, although others such as ethyl, propyl, may be present. Hydrocarbons and other species may also be present in varying concentrations, but usually at low levels.

TABLE 1

| Major Components of Chlorosilane Direct Process Residue (i) |
| --- |
| Components |
| 1,1,2-trichloro-1,2,2-trimethyldisilane |
| 1,2-dimethyl-1,1,2,2-tetrachlorodisilane |
| 1,2-dichloro-1,1,2,2-tetramethyldisilane |
| chloropentamethyldisilane |
| 1,3-dichloro-1,1,3,3-tetramethylcarbodisilane |
| 1,1,3-trichloro-1,3,3-trimethylcarbodisilane |
| 1,3-dimethyl-1,1,3,3-tetrachlorocarbodisilane |
| 1,3-dimethyl-1,1,3,3-tetrachlorodisiloxane |
| 1,3-dichloro-1,1,3,3-tetramethyldisiloxane |
| 1,1,3-trichloro-1,3,3-trimethyldisiloxane |
| dichlorodimethylsilane |
| methyltrichlorosilane |
| dichloroethylmethylsilane |
| $R(CH_3)SiCl_2 + R(CH_3)_2SiCl$, wherein R is ethyl, propyl, butyl, pentyl or hexyl |
| Solids |
| Al |
| Fe |
| Zn |
| Cu |
| Cl |

The hydrolysis of chlorosilane direct process residue (i) can be carried out in an acidic or basic medium to produce chlorosilane direct process residue hydrolyzed substrate (iii).

In one embodiment, the acidic aqueous medium comprises an acid selected from HCl and/or $HNO_3$.

In another embodiment, the basic aqueous medium comprises a base selected from the group consisting of calcium hydroxide, calcium oxide, sodium oxide, sodium hydroxide, potassium oxide, potassium hydroxide, magnesium oxide, magnesium hydroxide, calcium carbonate, calcium bicarbonate, sodium carbonate, sodium bicarbonate, magnesium carbonate, magnesium bicarbonate and combinations thereof.

In one specific embodiment, the process of reducing the level of chloride in chlorosilane direct process residue hydrolyzed substrate (iii) comprises contacting substrate (iii) with nitric acid for a time sufficient to reduce the chloride content to less than 1.8% by weight.

The amount of nitric acid to substrate (iii) is in the range of from 0.1:1 to 10:1 by weight to chlorosilane direct process residue hydrolyzed substrate (iii) on a dry basis, more specifically of from 1:1 to 10:1 by weight to chlorosilane direct process residue hydrolyzed substrate and most specifically of from 1:1 to 6:1 by weight to chlorosilane direct process residue hydrolyzed substrate (iii). The concentration of nitric acid is in the range of from 0.1% to 30% by weight, more specifically of from 1% to 20% by weight, and most specifically of from 1% to 10% by weight. Percent of dry solids is determined by placing a one gram sample of wet substrate (iii) in a 150° C. oven for 0.75 hours and comparing, the weight remaining after heating. The water content is typically about 50% for the total weight of the substrates.

The nitric acid is in contact with chlorosilane direct process residue hydrolyzed substrate (iii) for 1 to 6 hours, more specifically of from 1-3 hours, and most specifically of from 1-1.5 hours. The nitric acid is in contact with chlorosilane direct process residue hydrolyzed substrate (iii) at the temperature in the range of from 70 to 110° C., more specifically of from 80 to 100° C., and most specifically of from 80 to 90° C.

In certain embodiments, the process further comprises washing the acid or base hydrolyzed substrate with water to provide a hydrolyzate with an about 40% reduction in the level of chloride prior to contacting with nitric acid.

The amount of water employed is in the range of from 1:1 to 1000:1 by weight to chlorosilane direct process residue hydrolyzed substrate more specifically of from 1:1 to 500:1 by weight to chlorosilane direct process residue hydrolyzed substrate (iii), and most specifically of from 10:1 to 100:1 by weight to chlorosilane direct process residue hydrolyzed substrate (iii).

Without being bound by theory, it is believed that the nitric acid oxidizes the silicon-containing backbone of chlorosilane direct process residue hydrolyzed substrate (iii), thereby exposing the residual chemically-bound or physically-constrained chloride to water to aid in a more complete hydrolysis. Evidence of $NO_2$ and other reduced forms of $HNO_3$ as byproducts indicates that the oxidation reaction is occurring.

Various features of the invention are illustrated by the examples presented below.

Examples 1-15

Base hydrolyzed chlorosilane direct process residue substrates #1-#4 (BHS #1-#4) and acid hydrolyzed chlorosilane direct process residue substrates #1 and #2 (AHS #1 and #2) that contain different initial amounts of chloride are tested. The substrates were washed by stirring the wet hydrolyzed product with 100-fold weight of deionized water for one hour, filtering and an drying.

Example 1

A 100-mL 2-necked round bottom flask equipped with a magnetic stirbar, condenser, and thermocouple was charged with 9.2 grams of wet (50.5% solids; 4.6 grams of dry) (washed) base hydrolyzed substrate (BHS #1) and 46 grams of 10% nitric acid. The contents of the flask were heated to reflux (101° C.). At 48° C. the solids appeared to have foamed to twice the original size and at 87° C. a brown vapor of $NO_2$ was seen in the flask and condenser. Within 1½ hrs the $NO_2$ had dissipated and the reaction was cooled. The solid was filtered and the filtrate collected for chloride analysis. The solid was then washed with water until the pH of the filtrate was 7. The chloride level of the dried solid was measured by a sodium/potassium carbonate fusion followed by a silver nitrate titration and was found to be 0.29% (83% decrease) from the original value.

Examples 2-5

Examples 2-5 are conducted in similar manner as example 1 using base hydrolyzed substrate (BHS #1) and different treating conditions.

Example 6

A 100-mL 2-necked round bottom flask equipped with a magnetic stirbar, condenser, and thermocouple was charged with 4.88 grams of wet (50.5% solids; 2.46 grams of dry) (washed) base hydrolyzed substrate (BIB #1), 0.92 grams of $CaCl_2.H_2O$ (0.24 grams chloride) and 24.6 grams of 10% nitric acid. The chloride of the substrate was now 13.0%, consistent with many unwashed substrates. The contents of the flask were heated to 91° C. At 87° C. a brown vapor of $NO_2$ was seen in the flask and condenser. Within 2 hrs the $NO_2$ had dissipated and the reaction was cooled. The solid was filtered and the filtrate collected for chloride analysis. The solid was then washed with water until the pH of the filtrate was 7. The chloride level of the dried solid was measured by a sodium/potassium carbonate fusion followed by a silver nitrate titration and was found to be 1.03% (92% decrease) from the original value.

Examples 7-15

Examples 7-15 are conducted in similar manner as example 1 using different starting substrate and/or treating conditions. Table 2 summarizes the conditions and results of chloride reduction treatment.

TABLE 2

| | | Results of Post Treatments | | | | | | |
|---|---|---|---|---|---|---|---|---|
| Example | Substrate | Chloride Initial | Water Wash | Water: Substrate | Chloride post-wash | Nitric Acid Concentration | Acid: Substrate | Chloride Post $HNO_3$ Treatment |
| 1 | BHS #1 | 9.7% | 1 hour | 3.5:1 | 3.2% | 10% | 1:1 | 0.29% |
| 2 | BHS #1 | 9.7% | 1 hour | 3.5:1 | 3.2% | 10% | 6:1 | 0.13% |
| 3 | BHS #1 | 9.7% | 1 hour | 3.5:1 | 3.2% | 10% | 0.5:1 | 0.61% |

TABLE 2-continued

Results of Post Treatments

| Example | Substrate | Chloride Initial | Water Wash | Water: Substrate | Chloride post-wash | Nitric Acid Concentration | Acid: Substrate | Chloride Post $HNO_3$ Treatment |
|---|---|---|---|---|---|---|---|---|
| 4 | BHS #1 | 9.7% | 1 hour | 3.5:1 | 3.2% | 1% | 0.5:1 | 0.61% |
| 5 | BHS #1 | 9.7% | 1 hour | 3.5:1 | 3.2% | 1% | 0.3:1 | 0.65% |
| 6 | BHS #1 + $CaCl_2$ | 9.7% | n/a | n/a | 13.0% | 10% | 1:1 | 1.00% |
| 7 | BHS #2 no fines | 8.8% | 1 hour | 100:1 | 5.2% | 10% | 1:1 | 0.91% |
| 8 | BHS #3 | 12.0% | not washed | not washed | 12.0% | 10% | 1:1 | 1.00% |
| 9 | BHS #4 | | | | 1.0% | 10% | 6:1 | 0.14% |
| 10 | BHS #4 | 5.6% | 1 hour | 100:1 | 1.0% | 10% | 3:1 | 0.16% |
| 11 | BHS #4 | 5.6% | 1 hour | 100:1 | 1.0% | 10% | 1:1 | 0.21% |
| 12 | BHS #4 | 5.6% | 1 hour | 100:1 | 1.0% | 10% | 0.5:1 | 0.25% |
| 13 | BHS #4 | 5.6% | 1 hour | 100:1 | 1.0% | 1% | 0.1:1 | 0.49% |
| 14 | AHS #1- no fines | 13.1% | 1 hour | 100:1 | 7.8% | 10% | 1:1 | 1.8% |
| 15 | AHS #2- no fines | — | 15 min | 400:1 | — | 10% | 1:1 | 0.7% |

As can be seen from Table 2, the levels of chloride in the treated substrates are significantly reduced, mostly to less than 0.5%, even to less than 0.25%.

Headspace Analysis: In a separate experiment several hydrolyzed substrates were treated with 10% HO in 20 mL crimped-top vials suitable for headspace GC analysis. They were heated to 90° C. for one hour. Injection onto an Agilent GS-GASPRO (60 m×0.32 mm) GC column with electron ionization (70 eV) detection indicated the presence of NO, $N_2O$ and $CO_2$ for the substrates heated in the presence of an inert (nitrogen) environment. In an air environment, NO was not seen presumably due to oxidation to $NO_2$ which followed the same fate as in the experiments run in a nitrogen environment. The lack of $NO_2$ was explained by the immediate conversion of $NO_2$ to $HNO_3$ in the presence of water. Chlorine ($Cl_2$) was not observed.

Treatment of Model Compounds with $HNO_3$: Three compounds containing possible moieties in the hydrolyzed substrate were treated at 90° C. with 10% $HNO_3$ for one hour. The treated compounds and the headspace were analyzed by gas chromatography-mass spectral analysis spectrometry. The headspace analysis showed different results for the three compounds. $N_2O$ and $CO_2$ were observed for both the bis(trimethylsilyl)methane and hexamethyldisilane indicative of reduction of the nitric acid and oxidation (with bond breakage) of a carbon moiety. Bis(trimethylsilyl)methane had lower levels of $N_2O$ and $CO_2$ in the headspace than the hexamethyldisilane (250× and 30× lower respectively). GCMS analysis of the oxidized products corroborates the carbon-silicon and silicon-silicon bond breakage with the evidence of siloxanes for both substrates. There was no evidence of the nitric acid removing the chloromethyl group in either the head space or in the substrate analysis. These data indicate the possible mechanism by which nitric acid oxidizes the hydrolyzate backbone to expose unreacted chlorosilane. Table 3 shows the results of the experiments with model compounds.

TABLE 3

GC Results of Nitric Acid Treatment of Model Compounds

| Model Compound | Headspace GC Analysis | GCMS of Substrate |
|---|---|---|
| Chloromethylpentmethyl-disiloxane | no measurable peaks | loss of MM; composed of M' and MM' from SM |
| Bis(trimethylsilyl)methane | very low levels of $N_2O$ and $CO_2$ | MM, Hexamethyldisilane, Bis(trimethylsilyl)ethane |
| Hexamethyldisilane | $N_2O$ and $CO_2$ | MM, MDM, $MD_2M$, TMSO-pentamethyldisilane |

As a comparative example, washed BHS #1 was also treated with sulfuric acid, instead of nitric acid. The level of chloride was only reduced to 1.3% after the treatment.

TABLE 4

Comparison of Nitric Acid and Sulfuric Acid

| | Substrate | Chloride Initial | Water Wash | Water: Substrate | Chloride post-wash | Nitric Acid Concentration | Acid: Substrate | Chloride Post HNO3 Treatment |
|---|---|---|---|---|---|---|---|---|
| Example 1 | BHS #1 | 9.7% | 1 hour | 3.5:1 | 3.2% | 10% $HNO_3$ | 6:1 | 0.13% |
| Comparson 1 | BHS #1 | 9.7% | 1 how | 3.5:1 | 3.2% | 0% $HNO_3$ | 6:1 | 1.3% |

These examples are to be construed as exemplary in nature only and are not intended in any way to limit the appended claims. It is contemplated that a person having ordinary skill in the art would be able to produce obvious variations of the subject matter and disclosures herein contained that would be by reason of such ordinary skill within the literal or equitable scope of the appended claims.

What is claimed is:

1. A process for providing a low-chloride hydrolyzate comprising contacting an acid or base hydrolyzed substrate of a chlorosilane direct process residue with nitric acid to provide a hydrolyzate with a chloride content of less than about 1.8% by weight.

2. The process of claim 1 further comprising washing the acid or base hydrolyzed substrate with sufficient water to provide a hydrolyzate with an about 40% reduction in the level of chloride prior to contacting with nitric acid.

3. The process of claim 1 wherein the process provides for a hydrolyzate with a chloride content of less than about 0.5% by weight.

4. The process of claim 1 wherein the chlorosilane direct process residue contains at least one member selected from the group consisting of 1,1,2-trichloro-1,2,2-trimethyldisilane, 1,2-dimethyl-1,1,2,2-tetrachlorodisilane, 1,2-dichloro-1,1,2,2-tetramethyldisilane, chloropentamethyldisilane, 1,3-dichloro-1,1,3,3-tetramethylcarbodisilane, 1,1,3-trichloro-1,3,3-trimethylcarbodisilane, 1,3-dimethyl-1,1,3,3-tetrachlorocarbodisilane, 1,3-dimethyl-1,1,3,3-tetrachlorodisiloxane, 1,3-dichloro-1,1,3,3-tetramethyldisiloxane, 1,1,3-trichloro-1,3,3-trimethyldisiloxane, dichlorodimethylsilane, methyltrichlorosilane and dichloroethylmethylsilane.

5. The process of claim 1 wherein the chlorosilane direct process residue contains at least one member selected from the group consisting of $R(CH_3)SiCl_2$ and $R(CH_3)_2SiCl$, wherein R is ethyl, propyl, butyl, pentyl or hexyl.

6. The process of claim 1 wherein the amount of the nitric acid to the amount of dried acid or base hydrolyzed substrate is present in a ratio of from 0.1:1 to 10:1 by weight.

7. The process of claim 1 wherein the amount of the nitric acid to the amount of dried acid or base hydrolyzed substrate is present in a ratio of from 1:1 to 6:1 by weight.

8. The process of claim 1 wherein the nitric acid is present in an aqueous solution in the amount of from 0.1 to 30% by weight.

9. The process of claim 1 wherein the nitric acid is present in an aqueous solution in the amount of from 1 to 10% by weight.

10. The process of claim 1 wherein the nitric acid is in contact with the acid or base hydrolyzed substrate for at least 1 hour.

11. The process of claim 1 wherein the process is carried out at a temperature in the range of from about 70° C. to about 110° C.

12. The process of claim 1 wherein the process is carried out at a temperature in the range of from 80° C. to 90° C.

13. The process of claim 2 wherein the amount of water to the amount of acid or base hydrolyzed substrate is present in a ratio of from 1:1 to 1000:1 by weight.

14. The process of claim 2 wherein the amount of water to the amount of acid or base hydrolyzed substrate is present in a ratio of from 1:1 to 100:1 by weight.

* * * * *